United States Patent [19]

Rosauer

[11] 4,454,473
[45] Jun. 12, 1984

[54] SPINNING PROBE APPARATUS FOR INSPECTION OF BOLT HOLES AND THE LIKE

[75] Inventor: Peter J. Rosauer, Mount Prospect, Ill.

[73] Assignee: Magnaflux Corporation, Chicago, Ill.

[21] Appl. No.: 282,391

[22] Filed: Jul. 13, 1981

[51] Int. Cl.³ .................... G01R 33/00; F16H 35/00
[52] U.S. Cl. ............................ 324/262; 74/841; 74/842
[58] Field of Search .............. 324/221, 220, 219, 228, 324/233, 234, 237–242, 260; 74/840, 841, 842

[56] References Cited

U.S. PATENT DOCUMENTS 3,718,855 2/1973 Rogel et al. ............... 324/202
3,831,084 8/1974 Scalese et al. ............. 324/260

Primary Examiner—Gerard R. Strecker
Assistant Examiner—Warren S. Edmonds
Attorney, Agent, or Firm—Neuman, Williams, Anderson & Olson

[57] ABSTRACT

A probe utilizing electrical fields for nondestructive testing of metals is disclosed which is mounted in a hand-held portable housing, or head, having limit switches therein for restricting up and down movement of the probe. Apparatus for selectively engaging the limit switches by the probe driving mechanism, without injury to the internal parts of the head, is also disclosed. The head may be equipped with a slip ring extender also, to enable an operator to use the head in a variety of positions, and the depth setting mechanism for the probe is protected against inadvertent movement during continued usage of the head.

14 Claims, 13 Drawing Figures

U.S. Patent  Jun. 12, 1984  Sheet 1 of 4  4,454,473
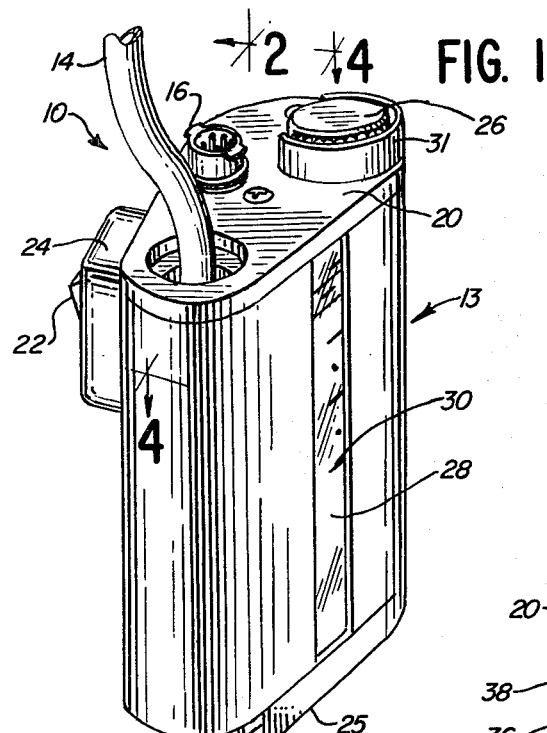
FIG. 1
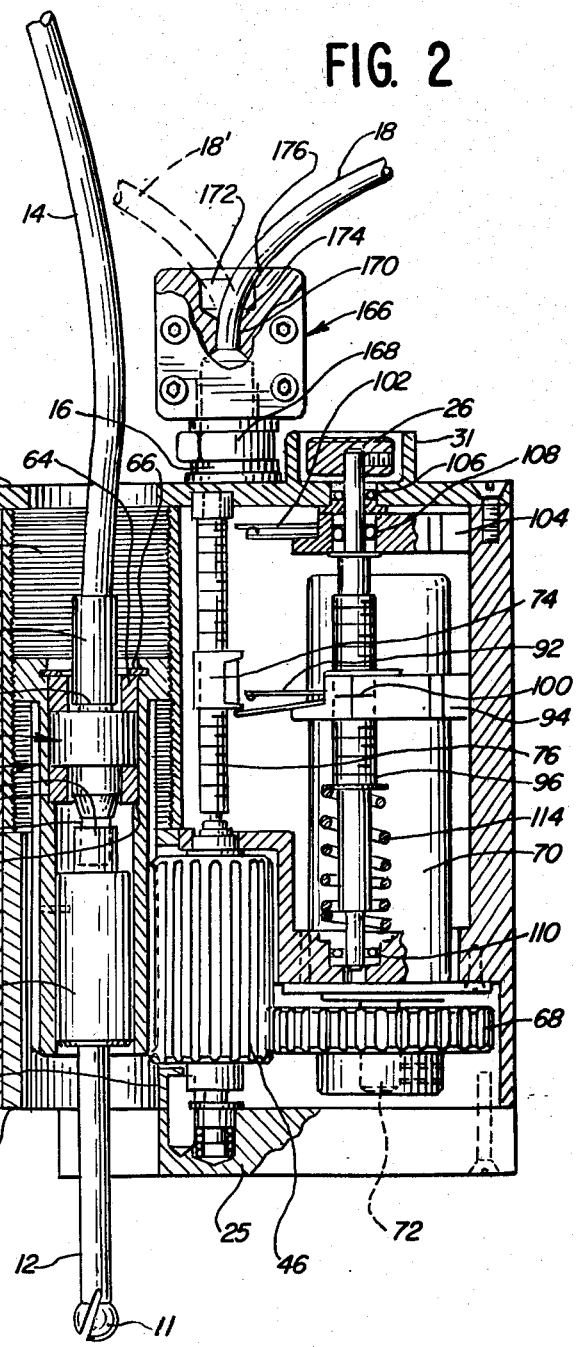
FIG. 2
FIG. 3

SPINNING PROBE APPARATUS FOR INSPECTION OF BOLT HOLES AND THE LIKE

This invention relates to apparatus for inspection of bolt holes or the like and more particularly to apparatus which is readily operable and can be easily, quickly and accurately adjusted to obtain a highly reliable indication of defects such as cracks which are in proximity to bolt holes. At the same time, the apparatus is very rugged and durable and capable of physically withstanding rough handling and usage and otherwise adverse operating conditions.

BACKGROUND OF THE INVENTION

Various types of probe support devices have heretofore been provided for effecting scanning movements of probes, for the inspection of inside surface portions of pipes or tubes or parts having bolt holes or the like through which fastening elements are extended. The Drummond et al U.S. Pat. No. 2,308,159 and also the Hastings et al U.S. Pat. No. 2,684,464 disclose devices in which a test coil structure is supported on a spindle which is operated through drive and gearing means for simultaneous rotational and axial movement of the test coil structure to trace a helical path within a tube or the like. Slip rings are used for transmission of electrical signals.

The Rogel et al U.S. Pat. No. 3,718,855 provides another disclosure of a device for moving the probe in a helical path, using drive and gearing means similar to the drive and gearing means of the Drummond et al and Hastings et al patents but differing therefrom in using a universal mounting bracket and a housing removably secured thereto.

Another arrangement is disclosed in the Scalese et al U.S. Pat. No. 3,831,084, also operative to effect a helical scan, but using a solenoid-operated plunger for selective control of rotation of a sleeve of the assembly. The Scalese et al patent shows limit switches used in a conventional manner to change the direction of movement or to stop rotation at limits of travel.

Such prior art types of probe support devices have been advantageously used to move an eddy current probe within a bolt hole. With an eddy current probe and with associated electronic instrumentation, as heretofore developed, the probes may be of very small size and it is possible to obtain highly accurate and reliable information as to the condition of the surface portion of a part around a bolt hole or the like, particularly with respect to the detection of cracks or other defects which might lead to failure of the part. Such information is extremely important in the testing of critical parts such as certain aircraft parts, for example.

For such applications, probe support devices of the prior art have been generally satisfactory, especially when carefully used. However, under certain conditions of use, they have been subject to malfunctions. When such have been detected, it has generally been the practice immediately to send the device to a shop having the necessary repair facilities and personnel to have the device repaired and to permit the testing operation to continue as promptly as possible. In such cases, valuable time may be lost. In other cases, malfunctions have escaped oftentimes to compromise the integrity of the testing operation.

SUMMARY OF THE INVENTION

This invention was evolved with the general object of improving the reliability, effectiveness and durability of probe support mechanisms while permitting quick and accurate adjustment thereof.

An important aspect of the invention is in the discovery of problems with prior art devices and causes of such problems. In one type of prior art device which uses drive and gearing means similar to those of the aforementioned patents, the limits of movement of the probe in an axial direction are defined by limit switches. The position of one of such limit switches, which defines the limit of inward movement of the probe, is adjustable by means of a thumbwheel and it has been discovered that the arrangement is such that the thumbwheel can, under certain conditions, be rotated to slip an adjustable stop past a wiper to result in a condition in which the only physical limit of travel of the wiper is a wall of the housing. The internal parts of the device may be damaged, so as to necessitate time-consuming repair procedures. Also, the malfunction may, in some cases, escape detection by the operator.

It has also been found that there is another problem which relates to electrical connections for supplying electrical power to a motor of the unit. It has been discovered that with movement of the device through various positions, and changing hands frequently while manipulating the device, the connection of a cable to the device may become damaged and as a result, either no power will be supplied to the device or the supply of power may be erratic.

A further problem has been found to exist with respect to the transmission of electrical signals to and from the probe. It has been found that prior devices have been unreliable, especially when used in positions which are inverted with respect to the conditions of normal use and that the reason for such unreliability resides in certain features of construction which can be changed to avoid the causes of the problem.

In accordance with the invention, a device is provided which overcomes these and other problems which have been discovered. An important feature of the device is in the provision of a device which incorporates non-jammable internal parts for setting the depth of a mechanically advanceable and retractable probe which may be an eddy current probe, for example.

In accordance with a specific feature, a limit switch is provided for restricting the travel of an eddy current probe, the switch being arranged to disconnect from the positioning mechanism before the switch becomes jammed against other parts in the head, or against the walls of the head.

Another important feature is in the provision of a device having an extension member for engaging either end of a slip ring intermediate a probe and an input and readout cable, thereby permitting use of the device in an upright or inverted position while maintaining the slip ring in its original upright position.

A further feature of the invention relates to the provision of a tripping mechanism for upward and downward probe limit switches, the tripping mechanism including a clutch which is disengageable for interrupting continued movement of the tripping mechanism after one of the limit switches has been activated.

Still another feature of the invention is in the provision of a thumbwheel adjustment mechanism for a stop member controlling the depth movement of the probe, and a protective shield for the thumbwheel to prevent accidentally misaligning the stop member during repeated movements of the head from one bolt hole to the next.

These and yet additional objects and features of the invention will become apparent from the following detailed discussion of an exemplary and an alternative embodiment, and from the attached drawings and appended claims.

In an apparatus for inspecting metal with an eddy current probe around a bolt hole, one form of the invention comprises a housing for the probe disposable over the bolt hole, and a probe carriage mounted in the housing. A motor mounted in the housing is provided with driving means which is connected to the carriage to drive it along the inside of the housing. A first limit switch is disposed within the housing for interrupting power from the motor to the carriage when the carriage has been moved a preselected distance. A movable stop means is mounted in the housing for determining the preselected distance of movement of the carriage and also to determine the point at which actuation of the first limit switch occurs. Mounting means for the stop means are located in the housing, and a mechanism is provided for disengaging and reengaging the stop means from the mounting means at the extremities of travel of the stop means.

BRIEF DESCRIPTION OF THE DRAWINGS

For a complete understanding of this invention, reference should be made to the accompanying drawings in which:

FIG. 1 is a perspective view of an eddy current scanner head housing for the present invention, including an eddy current probe extending from one end of the housing;

FIG. 2 is an enlarged sectional view of the scanner head housing shown in FIG. 1, partially in perspective, including a probe coupled to a slip ring disposed in the housing, taken along line 2—2 in FIG. 1, and adding, partly broken away, a strain relief plug attached to an electrical connector on top of the housing;

FIG. 3 is an inverted, enlarged sectional view, partially in perspective, of a portion of a scanner head which includes many of the same parts as the scanner head shown in FIG. 2, and also illustrating an alternate coupler mechanism for connecting the slip ring to the probe without disorienting the slip ring from its normally upright position;

DESCRIPTION OF PREFERRED EMBODIMENTS

Figure 4:
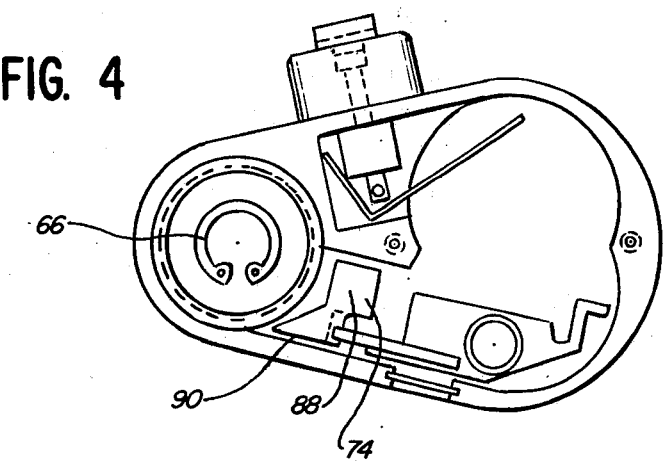
FIG. 4 is a top plan view of the scanner head shown in FIG. 1, taken along the line 4—4 in FIG. 1.

Reference numeral 10 generally designates a device constructed in accordance with the principles of the invention and particularly designed for the inspection of bolt holes in aircraft parts or the like, it being understood that the invention is not limited to bolt hole inspection and the various features of the invention may be applied in other applications.

The illustrated device 10 includes an eddy current probe 11 which is carried on the end of a support rod 12 for insertion into a bolt hole, the support rod 12 being rotated and simultaneously moved axially to effect a helical scan of the inside surface of a part about a bolt hole therein. The support rod 12 is connected through a slip ring assembly within a housing 13 to a cable 14 which is connected to suitable electronic instrumentation, not shown. An electrical connector 16 for a motor power cable 18 is located on a top end plate 20 of the housing 13. Operation of the device 10 is controlled by a switch operator 22 which is located in a housing 24 on one side of the housing 13.

In operation, the probe 11 may be inserted into a bolt hole while engaging an end wall 25 of the housing 13 with a surface of the part being inspected. Then the switch operator 22 may be actuated to one position whereupon the rod 12 is rotated and simultaneously moved axially to spin the probe 11 and move it into the bolt hole, scanning the inside surface which defines the bolt hole. When the probe 11 is moved inwardly to a certain limit position, a drive motor of the unit is automatically stopped and the switch operator 22 is then moved to a second position to cause the probe 11 to be withdrawn from the bolt hole and moved back to its initial position whereupon the motor of the unit is automatically de-energized. The depth of the limit position is adjustable by means of a thumbwheel 26 on the top end plate 20 of the housing 13. The limit depth position may be determined by looking through a transparent window 28 in a side wall of the housing 13, to view the position of a pointer with respect to a scale 30 formed by indicia marks on the window 28. A guard rail 31 is disposed on the top wall 20 and extends partly around the thumbwheel 26 to minimize the possibility of accidental engagement of the thumbwheel 26.

Figure 7:
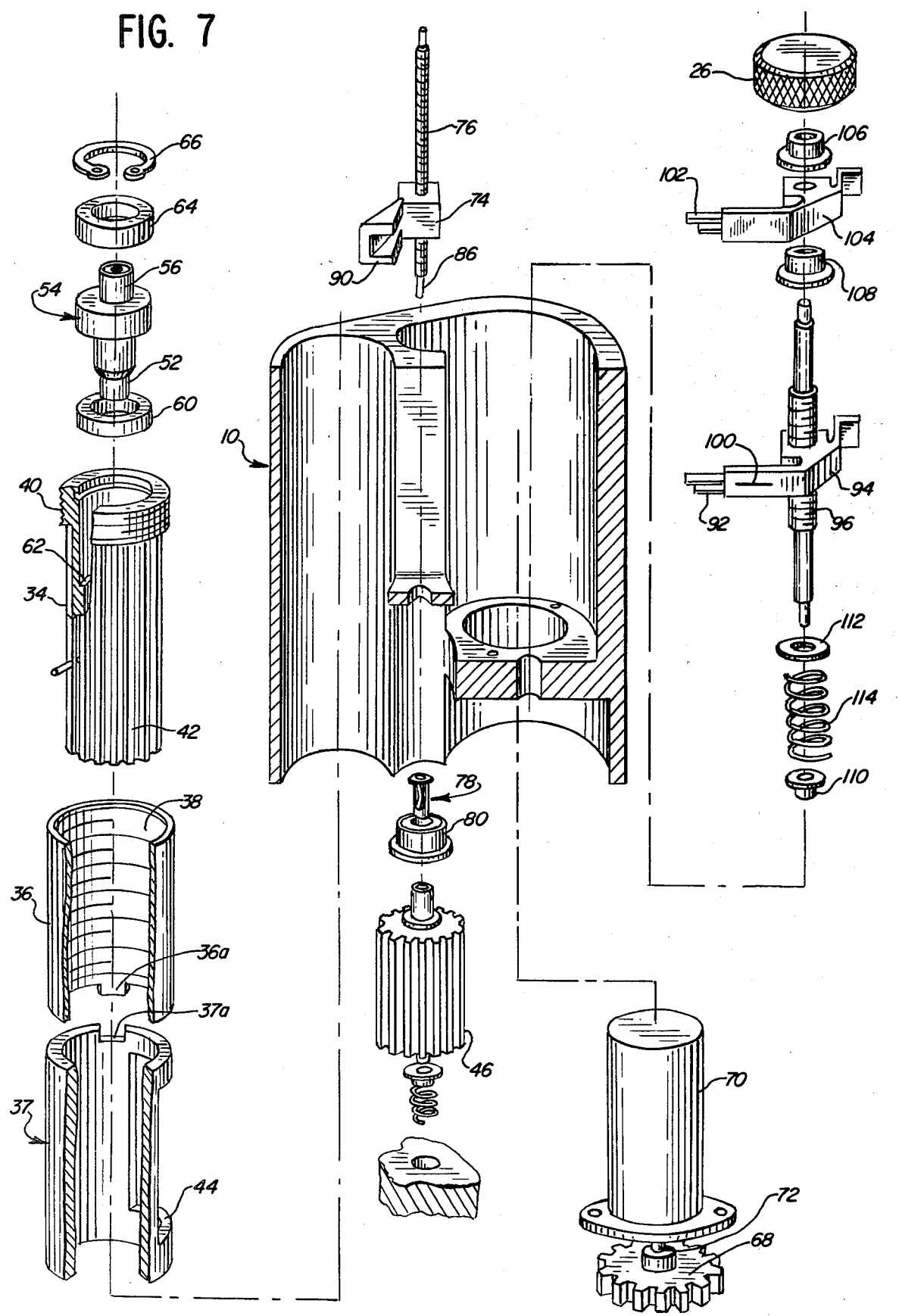
FIG. 7 is an exploded assembly view of the scanner head shown in FIG. 1, showing some of the apparatus partially broken away and in perspective.

With reference to FIGS. 2 and 7, the support rod 12 for the probe 11 is arranged in a carriage 34 for rotation and simultaneous axial movement into and out of a bolt hole. The carriage 34 is mounted in a sleeve having an upper portion 36 and a lower portion 37, both of which are fixed in the housing 13. The sleeve is open at both ends in order that the support rod 12 may be inserted into one end for connection to the cable 14 which is inserted from the other end. The cable end of the sleeve upper portion 36 (the upper end as illustrated) is internally threaded for a substantial distance as indicated by reference numeral 38 and cooperatively engages an externally threaded collar portion 40 of the carriage 34, so that as the carriage 34 is rotated, it is simultaneously moved axially.

Carriage 34 is formed with a set of external, peripheral gear teeth 42 which protrude through an opening 44 in the fixed lower sleeve portion 37 to be meshed with gear teeth formed on the outside of an idler pinion gear 46. When the idler gear 46 is rotated, the carriage 34 is also rotated and the carriage 34 is also moved axially through the interengagement of the external threads on the collar portion 40 with the internal threads 38 of the upper fixed sleeve portion 36. Accordingly, the eddy current probe 11 is moved in a helical path.

It is possible to construct the upper and lower sleeve portions 36 and 37 integrally with one another, so that the sleeve may be formed in one piece instead of two. However, such a one piece construction has been found in actual practice to bind the movement of the threads which are formed on the external surface of collar portion 40 as they move along the internal threads 38 of the sleeve. In order to combat that condition it was found that the sleeve should preferably be divided into upper and lower portions which are flexibly keyed together, as by one or more tabs 36a and one or more slots 37a (see FIG. 7). Such a construction permits the external threads on collar portion 40 to align themselves readily with the internal threads 38 in the upper sleeve portion 36.

The support rod 12 is fixed in a sleeve 48 which is, in turn, affixed within the carriage 34. The sleeve 48 supports a slip ring socket connector 50 which is adapted to receive the plug end 52 of a slip ring 54. Normally the assembly of the probe 11, support rod 12, sleeve 48 and connector 50 is formed as a unit and is inserted into the apparatus by pushing it through the carriage 34 until the connection 50 engages the plug end 52 of the slip ring 54. The upper end 56 of the slip ring is a plug which is grasped by a socket connector 58 disposed on the input/readout cable 14. The slip ring is formed with a rotatable mercury lubricated mechanical and electrical connection intermediate the upper end 56 and the plug end 52, so that the socket connector 58, when fixed upon the slip ring upper end 56, is not rotated during operation of the probe, although the plug end 52 is rotated.

The slip ring 54 is fastened into the carriage by a lower slip ring spacer 60 lodged against a shoulder 62 on the inside wall of the carriage, the slip ring being brought to rest upon the lower spacer 60 and sandwiched against the lower spacer by an upper slip ring spacer 64 and a spring clip 66.

Idler pinion gear 46, which drives the carriage, is driven itself by a drive gear 68 affixed to a motor 70 mounted inside the housing. Drive shaft 72 from the motor, together with drive gear 68 and idler pinion gear 46, forms a driving means connected to the carriage 34 for driving the carriage along the inside of the housing, thereby inserting the probe into a bolt hole or withdrawing the probe according to the direction of the motor.

Figure 9:
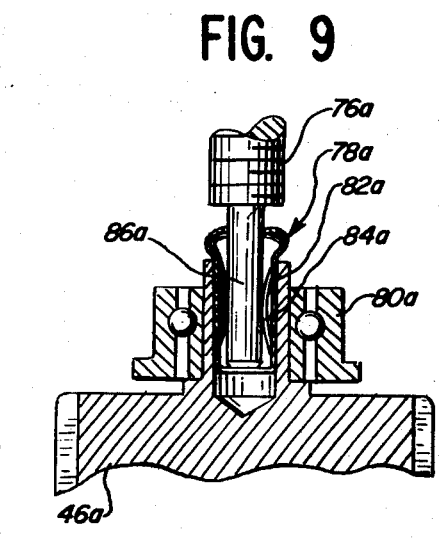
FIG. 9 is a sectional view on a larger scale of a portion of the scanner head shown in FIG. 8 taken along the line 9-9 in FIG. 8.

A trip nut 74 is mounted in a non-rotatable manner upon a threaded spindle 76 so that when the spindle is rotated, the trip nut will move vertically along the spindle. The spindle, in turn, is engaged upon idler pinion gear 46 by means of a spring clutch 78 and bearing 80. The clutch 78 may incorporate an outer cylindrical jacket, such as shown at 82a in FIG. 9, and an inner spring engagement surface, such as shown at 84a in FIG. 9, for frictionally grasping the reduced diameter end portion 86 of spindle 76. Thus, when the trip nut 74 becomes incidentally positioned against other portions of the probe housing or internal mechanism which is relatively fixed, the idler pinion gear 46 may continue to rotate without damaging the trip nut, or the threads of spindle 76, or any other portions of the probe housing internal parts. One manner of mounting the trip nut so that it is not rotatable about the spindle is to locate the spindle at a spindle mounting position 88 (see FIG. 4) adjacent an inner wall of housing 13. One side 90 of the trip nut is formed with a flat face which is adapted to ride along a flat portion of the inner wall of the housing, thus holding the nut against horizontal movement but permitting the threads of the spindle, which primarily form a track for the nut to follow, to carry the nut in a vertical direction.

Two limit switches are mounted inside the housing where they may be tripped when contacted by the trip nut 74. A first switch (not seen) having actuating arms 92 is incorporated in the body of a movable stop member 94 mounted upon a second threaded spindle 96. The movable stop member is also formed so that it bears against a portion of the inside wall of the housing 13 and thus is held from being rotatable about the second spindle. The body of the movable stop member is driven in a vertical direction on the threads of the second threaded spindle to wherever the operator of the probe determines to place it. Such placement is accomplished by turning thumbwheel 26 and rotating the second threaded spindle. As noted above, a position indicator mark or pointer 100 on the movable stop member is arranged to show through window 28, so that an operator can determine the position of the actuating arms 92 according to the relationship of the indicator mark or pointer 100 to the scale 30 which is formed by the window 28.

The first limit switch normally controls the distance which the probe travels "down" into a hole, or "outwardly" from the housing. Arms 92 on the first limit switch extend into the path of trip nut 74. Power from the motor causes gear 68 to drive the idler pinion gear 46, thus rotating spindle 76. When such rotation is in a direction to drive the trip nut toward the arms 92, and whenever the trip nut is thereby moved to contact and operate those arms, the first limit switch will be actuated and power from the motor, which also drives the probe carriage, will be interrupted. Thus, movement of the carriage for a distance in a direction controlled by the first limit switch, which distance is preselected by the person who operates the probe, will be halted. The probe is accordingly extended only as far as the movable limit switch permits it to go, pursuant to a determination by an operator.

A second limit switch (not seen) having actuating arms 102 limits the travel of the probe and carriage in the opposite direction, i.e., opposite to the direction limited by the first limit switch. Normally the second limit switch limits probe movement "upwardly" from a bolt hole, or "inwardly" through the housing. Fixed stop member 104 incorporates the second limit switch, and the actuating arms 102 extend from the switch into the path of the trip nut 74. Thus, the arms 102 will be moved when the trip nut is moved by rotation of the threaded spindle 76 and brought into contact with the arms. The direction in which spindle 76 rotates in order to bring the trip nut into contact with the arms 102 is opposite to the direction in which it rotates to bring the trip nut into contact with arms 92 on the movable limit switch.

The second limit switch, located in the body of fixed stop member 104, is arranged to interrupt power from the motor 70 to the carriage when the probe has reached a fully withdrawn position in the housing 10 in a manner similar to the manner by which the first limit switch interrupts power from the motor to the probe carriage.

Both sets of actuating arms 92 and 102 are made with flexible tip sections, bendable in either an upward or downward direction, so that they will not be injured if the stop nut 74 is accidentally moved along threaded spindle 76 past the actuating arm tips. If such movement should occur, it is only necessary to reverse the rotation of spindle 76 to bring the stop nut 74 back past the flexible arm tips so that it is once again disposed between the sets of arms.

The second threaded spindle 96 is installed (see FIG. 2) inside the housing 13 in a manner which permits the spindle to be moved downwardly and to avoid damage to the threads on it when the movable stop member 94 is adjusted against its maximum upward or downward limits. The upper end of spindle 96, which is connected to thumbwheel 26, is positioned in a pair of upper bearings 106 and 108, 106 being disposed through the top end plate 20 of the housing 10 and 108 being disposed through the fixed stop member 104. The thumbwheel 26 is attached to the second spindle 96 far enough from the outside surface of top end plate 20 to permit the spindle 96 to be drawn slightly into the housing. The lower, opposite end of spindle 96 is mounted in a lower bearing 110 inside housing 13, and a space below that bearing 110 is arranged so that spindle 96 can be pushed for a short distance into and through the lower bearing. Adjacent the lower end of the spindle, but spaced well apart from the lower bearing, a shoulder means such as washer 112 is loosely joined onto the spindle so that a coil spring 114 can be assembled about the spindle between the bearing 110 and the washer 112. The spring 114 is normally under slight compression so that it exerts pressure upwardly to maintain the upper end of the spindle and thumbwheel 26 in a firm disposition outside the housing 13.

In the arrangement of parts just described, it is possible to set the combined movable stop member and first limit switch at any desired location in order to limit the downward travel of the probe into a bolt hole. The probe operator simply rotates thumbwheel 26, which rotates the second threaded spindle 76, and moves the movable stop member up or down. The probe carriage 34 will be driven from the motor by gears 68 and 46 downwardly until trip nut 74 actuates arms 92 causing the first limit switch to shut the motor off. Similarly, when the direction of the motor, and consequently of the gears, is reversed, the probe carriage is moved upwardly until trip nut 74, driven by rotation of spindle 76, is raised up into contact with arms 102 and causes the second limit switch to again shut the motor off.

Occasionally a probe operator might attempt to change the location of the movable stop member 94 without realizing that it is already adjacent to its normal mechanical limits of travel on the threads of the second spindle 76. If the spindle were threaded completely from one end to the other, instead of being formed with diameters adjacent the end portions which are less than the diameter of the thread portion, as shown and described above, the operator's rotation of the thumbwheel too far in one direction or the other might cause serious damage to the threads, and ultimately to the measuring integrity of the probe itself. However, in the assembly of this invention, the threads are protected by the described arrangement which permits thread disengagement and reengagement at the maximum extremities of the movable stop member's travel, as follows:

When the movable stop member 94 is located near the fixed stop member, further turns of the thumbwheel will bring the first, movable stop member into contact with the fixed stop member 104. If the probe operator continues to rotate the thumbwheel, the threads on the second spindle 96 will cause that spindle to move downwardly against the pressure of spring 114 until the threads have become disengaged from the first stop member. Similarly, when the first stop member is near the lowest point of its travel, further turns of the thumbwheel 26 only result in driving the stop member 94 against the spring 114 until the stop member is completely driven off the threads. In either such disengagement, opposite rotation of spindle 76 thereafter results in immediate reengagement of the threads of movable stop member 94 onto the threads of spindle 96 due to the urging of spring 114. The foregoing disengagements and reengagements preserve and protect the threads inside the probe housing and prolong the life of the probe device.

Figure 5:
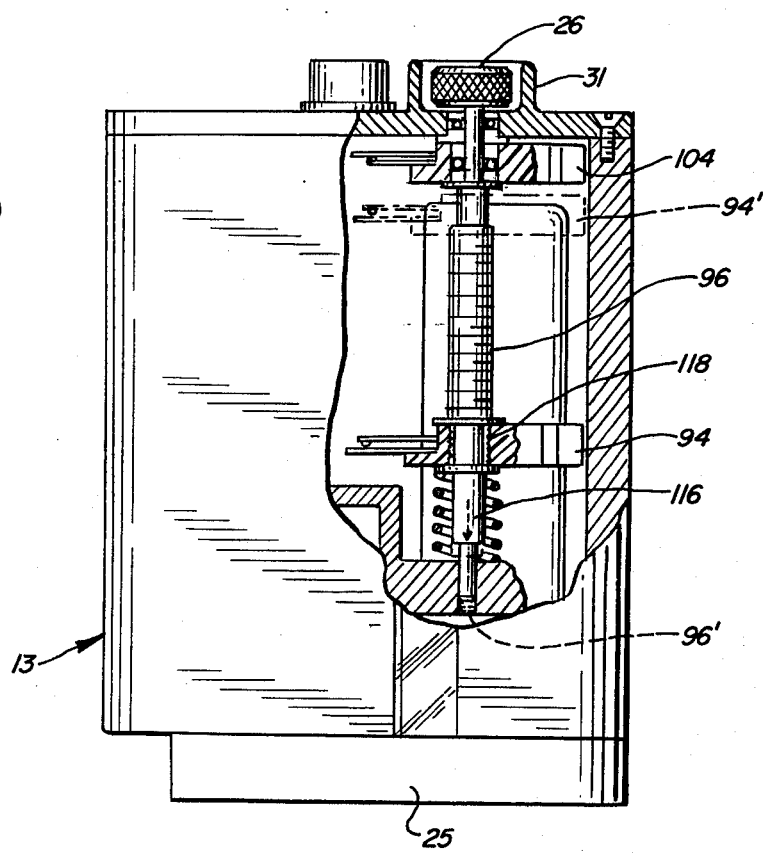
FIG. 5 is an elevational view partially broken away of the scanner head shown in FIG. 1.
Figure 6:
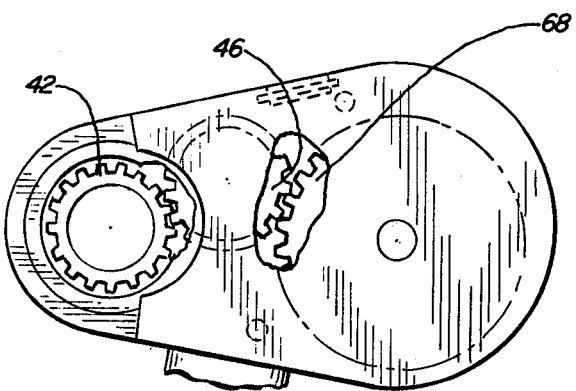
FIG. 6 is a bottom plan view partially broken away of the scanner head shown in FIG. 1.

In. FIG. 5, the uppermost position (dotted lines) and lowermost position (solid lines) of the movable stop 94 are illustrated, as well as the upper and lower locations of the second threaded spindle 96. In its lowermost position, the threaded spindle 96 is moved in the direction shown by dotted arrow 116 to the dotted line position 96' when the movable stop member 94 is moved to the dotted line position 94' against the upper, fixed stop 104. The solid lines of the spindle and movable stop illustrate the disposition of these members when the movable stop has been directed by its own internal threads 118 past the limits of the threads on spindle 96 to a point of disengagement of the threads from each other. Reengagement takes place when thumbwheel 26 is turned to rotate spindle 96 in a direction to reengage the threads 118 onto the thread portion of spindle 96.

Figure 8:
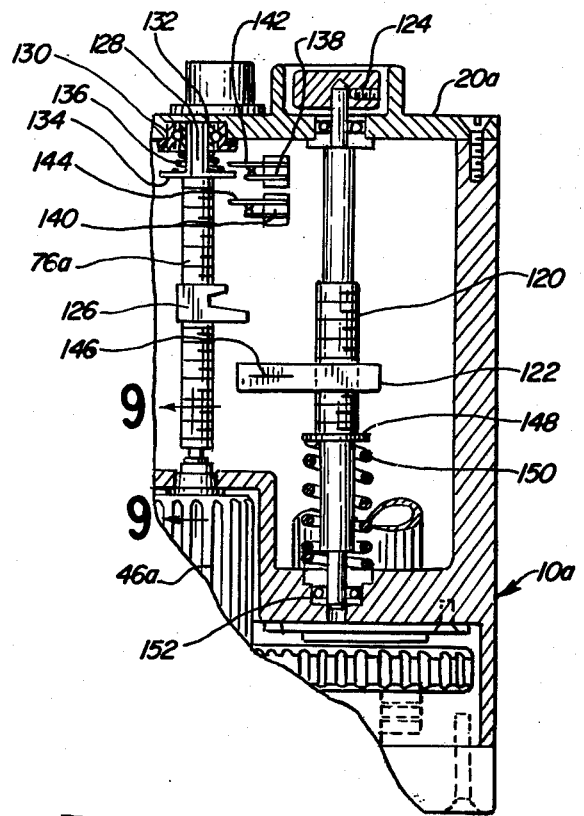
FIG. 8 is a sectional view partially in perspective of a portion of a scanner head like that shown in FIG. 1 but showing an alternative disposition of stop means and limit switches.

The same principle of disengagement and reengagement of a stop member on the second spindle is applied in the modified reorganization of parts shown in FIG. 8. A second threaded spindle 120 has a stop nut 122 mounted upon a threaded portion thereof. As is the case with the embodiment in FIG. 2, the stop is movable vertically by turning a thumbwheel 124. Stop nut 122 does not rotate around spindle 120 because it is restricted from such rotation, as by a flat side which rests against and is guided by a wall of the housing (not shown). A trip nut 126 is mounted upon a first threaded spindle 76a adjacent and opposite to the stop nut 122 on the second threaded spindle. The lower end of the first threaded spindle is mounted in a friction clutch engagement in the end of an idler pinion gear 46a in a manner identical to that shown in FIG. 7 and as referred to with respect to FIG. 9 above. The friction clutch engagement at the lower end 86a of the first spindle includes spring clutch 78a which is inserted into the center of bearing 80a. The upper, opposite end of the first threaded spindle 76a includes an upper, engagement pin portion 128. A bearing 130 mounted in the housing top end plate 20a is centrally apertured to receive a shaft mounting sleeve 132, which sleeve, in turn, receives the pin portion 128 of threaded shaft 76a and thus is engaged by the shaft. A circumferential collar 134 on sleeve 132 provides a bearing surface for mounting a helical spring 136 in slight compression between the collar 134 and bearing 130.

Two limit switches 138 and 140 are affixed to a wall of housing 10a near collar 134 and the trip nut 126 so that they can be activated and stop the motor in the housing as has been described generally in connection with the embodiment shown in FIG. 2. In the embodiment shown in FIG. 8, neither of the limit switches is movable in the sense of being relocatable to another point in the housing. Thus, no moving wire connection to either of the limit switches is necessary in the FIG. 8 embodiment.

The upper limit switch 138 in FIG. 8 acts to terminate downward movement of a probe carriage in the following manner: as idler pinion gear 46a rotates the first threaded spindle 76a in a direction to move the probe carriage downwardly, thereby directing a probe in the carriage down into a bolt hole, the trip nut 126 is moved along spindle 76a until it comes into contact with the stop nut 122. Since the trip nut can move no further at that point, the threads of spindle 76a force the spindle and its collar 134 upwardly against the force of spring 136 until the collar trips the activating arms 142 of limit switch 138, thereby shutting off power to the motor. When the probe is operated in the opposite direction, that is, by reversing the operational direction of the idler pinion gear 46a, the first threaded shaft 76a drives the trip nut 126 upwardly until a portion of the trip nut engages and activates arms 144 of the limit switch 140, again shutting off power to the motor.

Position indicator mark 146, the function of which is the same as indicator mark 100 in FIG. 2, is located on the movable stop nut 122 in FIG. 8. However, when a probe operator turns the thumbwheel 124 too far, the threaded shaft 120 becomes disengaged from the movable stop nut without damage to the threaded portions of either element. Trip nut 126 is disposed on the shaft 76a at a point where the stop nut 122, when it is raised to its upper limit of travel, will engage the trip nut, substantially ending upward movement of the stop nut 122 (when spring 136 becomes fully compressed), and requiring downward movement of the second threaded spindle 120 due to the turning of the threads of the spindle 120. The second threaded spindle 120 is thus moved against a washer 148 joined to the spindle, against helical spring 150 disposed about the lower end of the spindle, and moved further into bearing 152 in the housing at the lower end of spindle 122; in a manner identical to that illustrated in FIG. 2, the stop nut 122 becomes disengaged from the threaded portion of spindle 120 by running off the upper end of that portion. If the probe operater turns the thumbwheel too far in the opposite direction, the stop nut 122 becomes disengaged from the threaded portion of the spindle merely by being screwed off the lower end of the threaded portion of the spindle against the washer 148 and the helical spring 150.

Reengagement of the stop nut shown in FIG. 8 is obtained in a manner identical to that illustrated in FIG. 2, i.e., by rotating the thumbwheel 124 in a direction opposite to disengagement.

A probe apparatus containing either the arrangement of limit switches and stop means shown in FIG. 2, or containing an alternate arrangement as shown in FIG. 8, gains improved reliability in the regulation of helical movement of the probe through the housing, which is especially useful when the apparatus is in use for long periods of time on large areas containing many holes to be tested. The operation of such an apparatus, which includes either arrangement of limit switches and stop means, is also enhanced, in situations which require movement of the probe to be inverted, by providing apparatus to maintain the slip ring connector 54 in a substantially upright position. It has been found that the electrical continuity medium in the slip ring, normally mercury, tends to drain away from the contact surfaces within the slip ring when such a connector is used for an extended period of time in a position which is upside down to that shown in FIG. 2. An example of such use is on the underside of an airplane wing.

Accordingly, a slip ring inverter 154 (see FIG. 3) is interposed between the slip ring 54 and the body portion 48 of the probe. The inverter includes an upper portion 156 and lower portion 158, the former containing a plug 160 connecting the inverter to the body portion 48 of the probe assembly. The latter, i.e., lower portion 158, includes a receiving socket 162 into which plug 56 on the upper end of the slip ring 54 can be inserted to connect the slip ring with the probe assembly (FIG. 3). Also, the inverter 154 need not be removed from the probe assembly when the assembly and associated housing 13 are righted, and brought into the position shown in FIG. 2. In such event, the socket 58 on cable 14 is simply removed from the plug 52 on the slip ring, the slip ring is separated from the inverter, plug end 52 is inserted into the receiving socket 162, and socket 58, which is attached to the cable, is placed over the now-exposed upper end plug 56 of the slip ring, thus accomplishing inversion of the housing and probe while retaining constant orientation of the slip ring in the upright position shown in both FIGS. 3 and 2. Changing the orientation of the slip ring in the inverter by changing one end of the slip ring for the other in the inverter socket 162 is readily accomplished when the probe carriage is raised close to the top end plate 20 of the housing, thereby exposing an end of the inverter beyond the end of the tubular carriage 34, outside of the housing 13.

The thumbwheel 26 may be left in an exposed manner outside the housing in the top end plate 20, but without some degree of protection from accidental bumps and inadvertent rotations during extended handling and use of the probe apparatus the depth adjustment of the probe is likely to be changed. It is desirable, therefore, to provide a protective means such as the raised wall or guardrail 31 around most of the circumference of the thumbwheel (see FIGS. 1 and 2), thereby protecting it but also permitting ready adjustment and also providing for vertical movement of the second threaded spindle 96 when such movement is called for by spring 114.

Figure 10A:
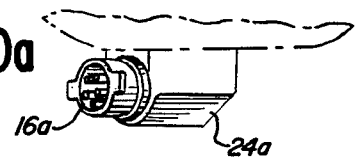
FIGS. 10a, 10b and 10c are perspective views of an embodiment of a switch and cable connection housing disposed on the side of a scanner head, which housing is an alternative to the switch housing on the scanner head shown in FIG. 1.
Figure 10B:
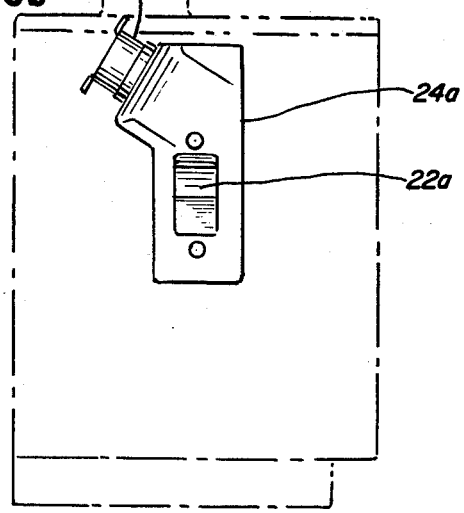
Figure 10C:
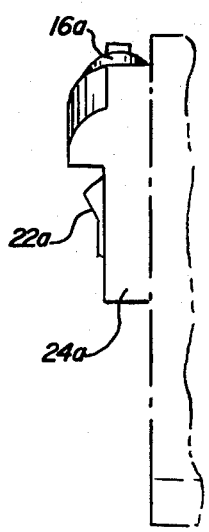

In addition to protecting the thumbwheel during extended periods of use of the probe, it is also desirable to provide a means of avoiding the making of sharp bends in the motor cable 18. Normally it is desirable to fasten such cable to connector 16 on the top end plate 20 of housing 13, near the point where the second cable 14 enters the housing, the two cables then being able to lend some common resistance to an operator's inadvertent attempts to make sharp bends in one cable or the other near the housing as the probe is being used. Alternatively, a switch 22a for the motor may be mounted in a box 24a affixed to the side of housing 13, with an angularly disposed connector 16a mounted alongside the toggle bar of the switch (FIGS. 10a, 10b, 10c); thus, when the housing of the probe is placed upon a horizontal surface, a connected power cord for the motor would not be required to make as sharp a bend next to the probe housing as if the cord were mounted in an unsupported manner on the housing top end plate.

A further alternative is to connect cable 18 to the motor through a strain relief plug 166. As shown in FIG. 2, the plug includes a second electrical connector 168 attached to the first electrical connection 16 on the housing 13. A passageway 170 inside the plug permits cable 18 to be joined to the second connector 168. Partway down into the passageway the walls surrounding it are provided with a large diameter opening 172 so that the lower portion of the passageway has a lesser diameter and first and second shoulders 174 and 176 of progressively wider separation are formed to engage the cable at spaced apart locations. The second shoulder 176 thus acts as a strain relief to prevent severe bending of cable 18 in the area of the first shoulder 174. When cable 18 is bent in different directions during use, as shown by two such locations 18 and 18' in FIG. 2, none of the engagements along shoulders 174 and 176 will be as much as 90°.

Figure 11:
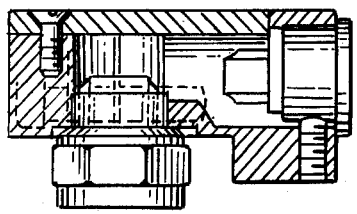
FIG. 11 is a sectional view, partially in perspective, of an alternative connector for the cable strain relief plug shown in FIG. 2 on top of the scanner head.

A still further alternative cable connecting device which may be utilized with the scanner head described above is shown in FIG. 11. When it is expected that the scanner head may be used in particularly close quarters where there would not be sufficient room to manipulate the head with the upwardly extending strain relief plug 166 attached, the 90° connector 178 shown in FIG. 11 may be used, in place of the plug 166. Connector 178 provides a low silhouette for accommodating tight quarters of operation and also provides a means for connecting a power cable, such as 18, to the probe housing without entailing any sharp bend in the cable during use. The 90° connector 178 is provided with a multi-socket plug 180 which is identical to the socket connector 168 shown in FIG. 2. The plug 180 is engageable upon the electrical connector 16 on the top plate 20 of the probe housing 13 which is shown in FIG. 1.

Plug 180 is mounted in a housing 182 which is provided with a cover plate 184 and a multi-pin receptacle 186 generally similar to connector 16. While the cover of the 90° connector 178 is off, exposing the interior of the connector housing, the sockets of plug 180 and the pins of receptacle 186 are connected. The plug 180 is then fixed in place in the housing, as with a set screw 188, and the receptacle 186 is fixed in place by means such as set screw 190. Thereafter, the cover plate 184 is attached with one or more screws 192.

Thus it will be seen that improvements have been provided in the construction of an apparatus for manipulating an eddy current probe in a plurality of dispositions. While particular embodiments of the present invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which come within the true spirit and scope of the invention.

What is claimed is:

1. Apparatus for inspecting metal by movement of a probe around a bolt hole comprising a housing for the probe disposable over the bolt hole, a probe carriage mounted in said housing, a motor mounted to said housing provided with driving means connected to said probe carriage for driving said probe carriage along the inside of said housing, trip means, track means in said housing connecting said trip means to said carriage for movement in a certain path in proportion to movement of said carriage, stop means, mounting means in said housing supporting said stop means in a position along said certain path, first and second limit switches connected in circuit with said motor for deenergizing said motor when operated, operating means for operating said first and second limit switches at certain relative positions of said trip and stop means to determine the limits of movement of said carriage, said operating means comprising switch actuating means extending outwardly from said limit switches, one of said switch actuating means being in the path of movement of said trip means, a limit switch actuating collar connected to said track means and disposed to intercept the other of said outwardly extending switch actuating means, said track means being movably mounted in said housing to urge said connected limit switch actuating collar into engagement with said other of said outwardly extending switch actuating means when the trip means engages the stop means.

2. Apparatus for inspecting metal by movement of a probe around a bolt hole comprising a housing for the probe disposable over the bolt hole, a probe carriage mounted in said housing, a motor mounted to the housing provided with driving means connected to said carriage for driving said carriage along the inside of said housing, trip means, track means in said housing connecting said trip means to said carriage for movement along a certain path in proportion to movement of said carriage, stop means, mounting means in said housing for supporting said stop means in a position along said certain path, said mounting means being arranged to effect adjustable movement of said stop means along said path between two limit positions, means for disengaging and reengaging said stop means from said mounting means at said two limit positions of said stop means, first and second limit switches connected in circuit with said motor for deenergizing said motor when operated, operating means for operating said first and second limit switches at certain relative positions of said trip and stop means to determine the limits of movement of said carriage, said switch operating means comprising switch actuating means extending outwardly from said limit switches, and a trip nut associated with said trip means and engageable with said outwardly extending switch actuating means of said first limit switch, said first limit switch being incorporated in said stop means.

3. Apparatus for inspecting metal by movement of a probe around a bolt hole comprising a housing for the probe disposable over the bolt hole, a probe carriage mounted in said housing, a motor mounted to the housing provided with driving means connected to said carriage for driving said carriage along the inside of said housing, trip means, track means in said housing connecting said trip means to said carriage for movement along a certain path in proportion to movement of said carriage, stop means, mounting means in said housing for supporting said stop means in a position along said certain path, said mounting means being arranged to effect adjustable movement of said stop means along said path between two limit positions, first and second limit switches connected in circuit with said motor for deenergizing said motor when operated, operating means for operating said first and second limit switches at certain relative positions of said trip and stop means to determine the limits of movement of said carriage, said switch operating means comprising switch actuating means extending outwardly from said limit switches, and a trip nut associated with said trip means and engageable with said outwardly extending switch actuating means of said first limit switch, said track means including an externally threaded spindle connected to said driving means of said motor, and said trip nut including an internally threaded portion for movably mounting said trip nut on said spindle.

4. Apparatus for inspecting metal by movement of a probe around a bolt hole comprising a housing for the probe disposable over the bolt hole, a probe carriage mounted in said housing, a motor mounted to the housing provided with driving means connected to said carriage for driving said carriage along the inside of said housing, trip means, track means in said housing connecting said trip means to said carriage for movement along a certain path in proportion to movement of said carriage, stop means, mounting means in said housing for supporting said stop means in a position along said certain path, said mounting means being arranged to effect adjustable movement of said stop means along said path between two limit positions, first and second limit switches connected in circuit with said motor for deenergizing said motor when operated, operating means for operating said first and second limit switches at certain relative positions of said trip and stop means to determine the limits of movement of said carriage, said mounting means for said stop means including a stop spindle having an externally threaded portion, and said stop means including a stop nut having an internally threaded aperture portion, said stop nut being disposed on said stop spindle with restricted rotation of said nut and with travel of said nut along said externally threaded portion of said stop spindle for a preselected distance being accomplished by rotation of said stop spindle.

5. The apparatus of claim 4 further comprising means for disengaging and reengaging said stop means from said mounting means including at least one portion of said stop spindle having a reduced diameter smaller than the diameter of said threaded portion of the stop spindle and smaller than said internally threaded aperture portion of said stop nut, and spring means arranged upon said stop spindle adjacent said spindle reduced diameter portion, said stop nut being movable against the bias of said spring means onto said reduced diameter portion of said stop spindle to disengage said internally threaded portion of said stop nut from said threaded portion of said stop spindle and after disengagement being movable for reengagement onto said threaded portion of said stop spindle in response to the bias of said spring means.

6. The apparatus of claim 5 in which said spring means is a coil spring arranged around one end of said stop spindle and extending between said housing and an engagement shoulder on said stop spindle, the one end of said stop spindle terminating in a pin stationed in a socket in said housing, said pin being movable further into said socket as said externally threaded portion of the spindle is urged toward said socket against the bias of said spring.

7. The apparatus of claim 4 in which said stop spindle is mounted in a slip-fitting shaft mounting means in said housing.

8. The apparatus of claim 7 in which said slip-fitting shaft mounting means is a clutch frictionally engaging one end of said stop spindle.

9. Apparatus for inspecting metal by movement of a probe around a bolt hole comprising a housing for the probe disposable over the bolt hole, a probe carriage mounted in said housing, a motor mounted to said housing provided with driving means connected to said probe carriage for driving said probe carriage along the inside of said housing, trip means, track means in said housing connecting said trip means to said carriage for movement in a certain path in proportion to movement of said carriage, stop means, mounting means in said housing supporting said stop means in a position along said certain path, first and second limit switches connected in circuit with said motor for deenergizing said motor when operated, operating means for operating said first and second limit switches at certain relative positions of said trip and stop means to determine the limits of movement of said carriage, said probe carriage including a connecting means arranged for transmitting electrical signals from a first end thereof to a second end thereof, said first end being rotatably disposed relative to said second end, a first coupling means for coupling said first end of said connecting means to an eddy current cable, a second coupling means for connecting said second end of said connecting means to a probe assembly, and a connecting means inverter disposed intermediate said second coupling means and the probe assembly, said inverter being provided with a receiving means for selectively attaching said first coupling means or said second coupling means onto the inverter, said connecting means including a slip ring, said probe carriage further including a tubular casing rotatably mounted inside said housing, said inverter being fixed inside said tubular casing and extendable outwardly therefrom through one end of said tubular casing, said first coupling means and said second coupling means being selectively disposable in said inverter receiving means adjacent said one end of said tubular casing.

10. Apparatus for inspecting metal by movement of a probe around a bolt hole comprising a housing for the probe disposable over the bolt hole, a probe carriage mounted in said housing, a motor mounted to said housing provided with driving means connected to said probe carriage for driving said probe carriage along the inside of said housing, trip means, track means in said housing connecting said trip means to said carriage for movement in a certain path in proportion to movement of said carriage, stop means, mounting means in said housing supporting said stop means in a position along said certain path, said mounting means being arranged to effect adjustable movement of said stop means along said path between two limit positions, means for engaging and disengaging said stop means to and from said mounting means at said two limit positions of said stop means, first and second limit switches connected in circuit with said motor for deenergizing said motor when operated, operating means for operating said first and second limit switches at certain relative positions of said trip and stop means to determine the limits of movement of said carriage and to obtain a preselected distance of movement thereof, said movable stop means extending outside the housing and including adjustment means adjacent the housing for setting the preselected distance of movement of said carriage, and protective means disposed on the housing to screen said adjustment means from dislocation.

11. The apparatus of claim 10 in which said protective means is a raised wall on said housing partially surrounding said adjustment means.

12. Apparatus for inspecting metal by movement of a probe around a bolt hole comprising a housing for the probe disposable over the bolt hole, a probe carriage mounted in said housing, a motor mounted to the housing provided with driving means connected to said carriage for driving said carriage along the inside of said housing, trip means, track means in said housing connecting said trip means to said carriage for movement along a certain path in proportion to movement of said carriage, stop means, mounting means in said housing for supporting said stop means in a position along said certain path, said mounting means being arranged to effect adjustable movement of said stop means along said path between two limit positions, first and second limit switches connected in circuit with said motor for deenergizing said motor when operated, operating means for operating said first and second limit switches at certain relative positions of said trip and stop means to determine the limits of movement of said carriage, a first electrical connector for a power cable to said motor mounted on a first face of said housing, a switch for controlling electrical power to said motor mounted upon a face of said housing adjacent to said first face thereof, and a cable strain relief plug comprising second electrical connector engaged upon said first connector on the first face of the housing, a passageway formed in said relief plug extending from said second connector through a body portion of said plug, and first and second shoulder means formed in said body portion of the plug adjacent and around the passageway, said first shoulder means being disposed in a circumference around said passageway of lesser diameter than the second shoulder means.

13. The apparatus of claim 12 in which said first and second shoulder means are respectively and successively engageable upon an electrical cable extending from said second connector through said passageway in said plug.

14. Apparatus for inspecting metal by movement of a probe around a bolt hole comprising a housing for the probe disposable over the bolt hole, a probe carriage mounted in said housing, a motor mounted to the housing provided with driving means connected to said carriage for driving said carriage along the inside of said housing, trip means, track means in said housing connecting said trip means to said carriage for movement along a certain path in proportion to movement of said carriage, stop means, mounting means in said housing for supporting said stop means in a position along said certain path, said mounting means being arranged to effect adjustable movement of said stop means along said path between two limit positions, first and second limit switches connected in circuit with said motor for deenergizing said motor when operated, operating means for operating said first and second limit switches at certain relative positions of said trip and stop means to determine the limits of movement of said carriage, a first electrical connector for supplying power to said motor, said first electrical connector being mounted on a first face of said housing, a switch for controlling electrical power to said motor mounted upon a face of said housing adjacent to said first face thereof, and a second electrical connector arranged to be secured to said first electrical connector and including a housing, a multi-terminal plug in said housing of said second electrical connector for engaging a socket of said first electrical connector, and a multi-terminal receptacle connected to said multi-terminal plug inside said housing of said second electrical connector and disposed therein in a position facing away from said plug at a sharp angle.

* * * * *